United States Patent [19]

Theodoridis

[11] Patent Number: 5,441,925
[45] Date of Patent: * Aug. 15, 1995

[54] 1-AMINO-3-(BICYCLIC HETEROCYCLYL)-6-FLUOROALKYLURACILS

[75] Inventor: George Theodoridis, Princeton, N.J.

[73] Assignee: FMC Corporation, Philadelphia, Pa.

[*] Notice: The portion of the term of this patent subsequent to Aug. 13, 2010 has been disclaimed.

[21] Appl. No.: 267,271

[22] Filed: Jun. 28, 1994

[51] Int. Cl.⁶ .................. A01N 43/42; C07D 401/02
[52] U.S. Cl. ...................................... 504/243; 544/310
[58] Field of Search ......................... 544/310; 504/243

[56] References Cited

U.S. PATENT DOCUMENTS

| | | | |
|---|---|---|---|
| 5,127,935 | 7/1992 | Satow et al. | 544/310 |
| 5,232,898 | 8/1993 | Suchy et al. | 544/310 |
| 5,310,723 | 5/1994 | Theodoridis | 544/310 |

FOREIGN PATENT DOCUMENTS

| | | | |
|---|---|---|---|
| 476697 | 3/1992 | European Pat. Off. | 544/310 |
| 15057 | 12/1990 | WIPO | 544/310 |

*Primary Examiner*—Cecilia Tsang
*Attorney, Agent, or Firm*—H. Robinson Ertelt; Robert M. Kennedy

[57] ABSTRACT

Herbicidal 1-Amino-3-(bicyclic heterocyclyl)-6-fluoroalkyluracils of the formula

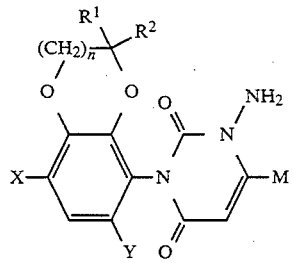

in which M is fluoroalkyl($C_{1-6}$); $R^1$ is hydrogen or alkyl($C_{1-6}$); $R^2$ is hydrogen or alkyl ($C_{1-6}$); Y is hydrogen, fluorine, chlorine, or bromine; X is hydrogen, fluorine, chlorine, bromine, cyano, alkyl($C_{1-6}$), or fluoroalkyl($C_{1-6}$); and n is 0 or 1.

13 Claims, No Drawings

1-AMINO-3-(BICYCLIC HETEROCYCLYL)-6-FLUOROALKYLURACILS

This invention relates to uracil compounds useful as herbicides, and to intermediates useful for producing herbicides. More particularly the present invention pertains to 1-amino-3-(bicyclic heterocyclyl)-6-fluoroalkyluracils, methods of preparing them, their intermediates, their compositions, and methods of destroying unwanted plants by preemergence or post-emergence application of the herbicidal compositions to the locus where control is desired. The herbicidal compounds of this invention may be used to effectively control a variety of grassy or broad leaf plant species. The compounds of this invention have the following structure:

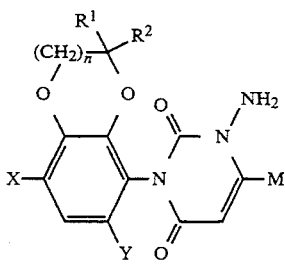

in which

M is fluoroalkyl ($C_{1-6}$, preferably $C_{1-3}$, more preferably $C_1$) having 1 to 6 fluorines;

$R^1$ is hydrogen or alkyl($C_{1-6}$, preferably $C_{1-3}$; more preferably $C_1$);

$R^2$ is hydrogen or alkyl ($C_{1-6}$, preferably $C_{1-3}$; more preferably $C_1$);

Y is hydrogen, fluorine, chlorine, or bromine;

X is hydrogen, fluorine, chlorine, bromine, cyano, alkyl($C_{1-6}$, preferably $C_{1-3}$, more preferably $C_1$), or fluoroalkyl($C_{1-6}$, preferably $C_{1-3}$, more preferably $C_1$) having 1 to 6 fluorines; and n is 0 or 1.

My application, Ser. No. 107,097, filed Aug. 13, 1993, now U.S. Pat. No. 5,346,881, the contents of which are hereby incorporated by reference, discloses similar compounds in which the 1-substituent of the uracil ring is selected from a variety of groups other than amino.

Preferred compounds of the present invention include those in which M is trifluoromethyl or pentafluoroethyl; $R^1$ is hydrogen, methyl, or ethyl; $R^2$ is hydrogen, methyl, or ethyl; X is chlorine or bromine; Y is hydrogen, chlorine, or fluorine; and n is 0 or 1. Compounds that are more preferred include those in which M is trifluoromethyl; $R^1$ is hydrogen or methyl; $R^2$ is hydrogen or methyl; X is chlorine or bromine; Y is hydrogen, chlorine, or fluorine; and n is 0 or 1.

Compounds that are particularly preferred include -1-amino-3-(7-chloro-2,2-dimethyl-5-fluoro- 1,3-benzodioxol-4-yl)-6-trifluoromethyluracil; 1-amino-3-(7-bromo-2,2-dimethyl-5-fluoro- 1,3-benzodioxol-4-yl)-6-trifluoromethyluracil; 1-amino-3-(8-chloro-1,4-benzodioxan-5-yl)-6-trifluoromethyluracil; 1-amino-3-(8-bromo-6-fluoro-1,4-benzodioxan-5-yl)-1-methyl-6-trifluoromethyluracil; 1-amino-3-(8-chloro-6-fluoro-1,4-benzodioxan-5-yl)-6-trifluoromethyluracil; 1-amino-3-(6,8-dichloro-1,4-benzodioxan-5-yl)-6-trifluoromethyluracil; and 1-amino-3-(7-chloro-2,2-dimethyl-1,3-benzodioxol-4-yl)-6-trifluoromethyluracil.

Representative compounds of this invention are listed in the Table. The compounds of this invention may be prepared from commercially available starting materials or those the synthesis of which is known in the art or using modifications thereof that are within the skill of the art. The methods are described more particularly in my application referenced above and in the following Example.

EXAMPLE

SYNTHESIS OF 1-AMINO-3-(7-CHLORO-2,2-DIMETHYL-5-FLUORO-1,3-BENZODIOXOL-4-YL)-6-TRIFLUOROMETHYLURACIL (Compound 2)

Step A Synthesis of O-(2,4-dinitrophenyl)hydroxylamine as an intermediate

To a suspension of 2.0 g (0.0074 mole) of ethyl N-(2,4-dinitrophenoxy)acetimidate in 10 mL of dioxane, cooled in an ice/water bath, was added dropwise 3 mL of 70% perchloric acid during a 10 minute period. The reaction mixture was stirred at 0°–5° C. for five hours and then was poured into 100 mL of ice water. This mixture was extracted three times with 40 mL of methylene chloride. The combined extracts were dried over anhydrous magnesium sulfate and filtered. The solvent was evaporated from the filtrate under reduced pressure, leaving 2.8 g of a brown oil. This oil was dissolved in 20 mL of diethyl ether, and 30 mL of petroleum ether was added to the solution, causing a precipitate to form. This precipitate was recovered by filtration. After being washed with petroleum ether and dried, 0.75 g of O-(2,4-dinitrophenyl)hydroxylamine was recovered as a yellow powder. The NMR spectrum was consistent with the proposed structure. This method is described by Y. Tamura et al., *J. Org. Chem.*, 38, 1239 (1973).

Step B Synthesis of 1-amino-3-(7-chloro-2,2-dimethyl-5-fluoro-1,3-benzodioxol-4-yl)-6-trifluoromethyluracil In a flask 0.49 g (0.0013 mole) of 3-(7-chloro-2,2-dimethyl-5-fluoro-1,3-benzodioxol-4-yl)-6-trifluoromethyluracil (prepared as in Example 1, Steps A to H of my application referenced above, except that the intermediate product is isolated before reaction with potassium carbonate and methyl iodide) and 0.21 g (0.0015 mole) of potassium carbonate in 30 mL of N,N-dimethylformamide are heated at 60° C. for 20 minutes. This solution is then cooled to 25° C. at which temperature 0.30 g (0.0015 mole) of O-(2,4-dinitrophenyl)hydroxylamine is added. This mixture is stirred for approximately 18 hours after which it is poured into 100 mL of ice water. The mixture is extracted three times with 40 mL of methylene chloride. The combined extracts are dried over anhydrous magnesium sulfate. After being filtered, the solvent is evaporated from the extract under reduced pressure, yielding 1-amino-3-(7-chloro-2,2-dimethyl-5-fluoro-1,3-benzodioxol-4-yl)-6-trifluoromethyluracil.

HERBICIDAL ACTIVITY

The 1-amino-3-(bicyclic heterocyclyl)-6-fluoroalkyluracils herbicides of this invention are tested for pre- and post-emergence herbicidal activity using a variety of crops and weeds. The test plants include soybean (*Glycine max* var. Williams), field corn (*Zea mays* var. Agway 425X), wheat (*Triticum aestivum* var. Wheaton), morningglory (*Ipomoea lacunosa* or *Ipomoea hederacea*), velvetleaf (*Abutilon theophrasti*), green foxtail (*Setaria viridis*), Johnsongrass (*Sorghum halepense*), blackgrass (*Aloepecurus myosuroides*), common chickweed (*Stellaria media*), and common cocklebur (*Xanthium pensylvanicum*).

For preemergence testing, two disposable fiber flats (8 cm×15 cm×25 cm) for each rate of application of each candidate herbicide are filled to an approximate depth of 6.5 cm with steam-sterilized sandy loam soil. The soil is leveled and impressed with a template to provide five evenly spaced furrows 13 cm long and 0.5 cm deep in each flat. Seeds of soybean, wheat, corn, green foxtail, and Johnsongrass are planted in the furrows of the first flat, and seeds of velvetleaf, morningglory, common chickweed, cocklebur, and blackgrass are planted in the furrows of the second flat. The five-row template is employed to firmly press the seeds into place. A topping soil of equal portions of sand and sandy loam soil is placed uniformly on top of each flat to a depth of approximately 0.5 cm. Flats for postemergence testing are prepared in the same manner except that they are planted 8–12 days prior to the preemergence flats and placed in a greenhouse and watered, thus allowing the seeds to germinate and the foliage to develop. In both pre- and postemergence tests, a stock solution of the candidate herbicide is prepared by dissolving 0.27 g of the compound in 20 mL of water/acetone (50/50) containing 0.5% v/v sorbitan monolaurate. For an application rate of 3000 g/ha of herbicide a 10 mL portion of the stock solution is diluted with water/acetone (50/50) to 45 mL. The volumes of stock solution and diluent that may be used to prepare solutions for lower application rates are shown in the following table:

| Application Rate (g/ha) | Volume of Stock Solution (mL) | Volume of Acetone/Water (mL) | Total Volume of Spray Solution (mL) |
| --- | --- | --- | --- |
| 3000 | 10 | 35 | 45 |
| 900 | 3 | 42 | 45 |
| 300 | 1 | 44 | 45 |
| 90 | 0.3 | 35 | 45.3 |
| 30 | 0.1 | 45 | 45.1 |
| 9 | 0.03 | 45 | 45.03 |
| 3 | 0.01 | 45 | 45.01 |

The preemergence flats are initially subjected to a light water spray. The four flats are placed two by two along a conveyor belt (i.e., the two preemergence followed by the two postemergence flats). The conveyor belt passes under a spray nozzle mounted about ten inches above the post-emergent foliage. The preemergent flats are elevated on the belt so that the soil surface is at the same level below the spray nozzle as the foliage canopy of the postemergent plants. The spray of herbicidal solution is commenced and once stabilized, the flats are passed under the spray at a speed to receive a coverage equivalent of 1000 L/ha. At this coverage the application rates are those shown in the above table for the individual herbicidal solutions. The preemergence flats are watered immediately thereafter, placed in the greenhouse and watered regularly at the soil surface. The postemergence flats are immediately placed in the greenhouse and not watered until 24 hours after treatment with the test solution. Thereafter they are regularly watered at ground level. After 17–21 days the plants are examined and the phytotoxicity data recorded.

For herbicidal application, the 1-amino-3-(bicyclic heterocyclyl)-6-fluoroalkyluracils are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and post-emergence herbicides, are in the form of finely divided particles which disperse readily in water or other dispersants. The wettable powder is ultimately applied to the soil either as a dry dust or as an emulsion in water or other liquid. Typical carriers for wettable powders include Fuller's earth, kaolin clays, silicas, and other highly absorbent, readily wettable inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, 1.0 part of sodium lignosulfonate, and 0.3 part of sulfonated aliphatic polyester as wetting agents. Frequently additional wetting agent and/or oil will be added to the tank mix for postemergence application to facilitate dispersion on the foliage and absorption by the plant.

Other useful formulations for herbicidal applications are emulsifiable concentrates (ECs) which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include suspensions of the active ingredient in a relatively non-volatile solvent such as water, corn oil, kerosene, propylene glycol, or other suitable solvents.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form by a propellant, such as carbon dioxide, propane or butane, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The 1-amino-3-(bicyclic heterocyclyl)-6-fluoroalkyluracils of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, for example, about 4 to 300 g/ha to, preferably about 10 to 30 g/ha. For field use, where there are losses of herbicide, higher application rates (for example, four times the rates mentioned above) may be employed.

The 1-amino-3-(bicyclic heterocyclyl)-6-fluoroalkyluracils of this invention may be used in combination with other herbicides, for example they may be mixed with, say, an equal or larger amount of a known herbicide such as aryloxyalkanoic acid herbicides such as (2,4-dichlorophenoxy)acetic acid (2,4-D), (4-chloro-2-methylphenoxy)acetic acid (MCPA), (+/−)-2-(4-chloro-2-methylphenoxy)propanoic acid (MCPP); urea herbicides, such as N,N-dimethyl-N'-[4-(1-methylethyl)phenyl]urea (isoproturon); imidazolinone herbicides, such as 2-[4,5-dihydro-4-methyl-4-(1-methylethyl)-5-oxo-1H-imidazol-2-yl]-3-pyridinecarboxylic acid (imazapyr), a reaction product comprising (+/−)-2-[4,5-dihydro-4-methyl-4-(1-methylethyl)-5-oxo-1H-imidazol-2-yl]-4-methylbenzoic acid and (+/−)-2-[4,5-dihydro-4-methyl-4-(1-methylethyl)-5-oxo-1H-imidazol-2-yl]-5-methylbenzoic acid (imazamethabenz), (+/−)-2-[4,5-dihydro-4-methyl-4-(1-methyl-ethyl)-5-oxo-1H-imidazol-2-yl]-5-ethyl-3-pyridinecarboxylic acid (imazethapyr), and (+/−)-2-[4,5-dihydro-4-methyl-4-(1-methylethyl)-5-oxo-1H-imidazol-2-yl]-3-quinolinecarboxylic acid (imazaquin); diphenyl ether herbicides, such as 5-[2-chloro-4-(trifluoromethyl)phenoxy]-2-nitrobenzoic acid (acifluorfen), methyl 5-(2,4-dichlorophenoxy)-2-nitrobenzoate (bifenox), and 5-[2-chloro-4-(trifluoromethyl)phenoxy]-N-(methylsulfonyl)-2-nitrobenzamide (fomasafen); hydroxybenzonitrile herbicides, such as 4-hydroxy-3,5-diiodobenzonitrile (ioxynil), and 3,5-dibromo-4-hydroxybenzonitrile (bromoxynil); sulfonylurea herbicides, such as 2-[[[[(4-chloro-6-methoxy-2pyrimidinyl)amino]carbonyl]amino]sulfonyl]benzoic acid (chlorimuron), 2-chloro-N-[[(4-methoxy-6-methyl-1,3,5-triazin-2-yl)amino]carbonyl]benzenesulfonamide (chlorsulfuron), 2-[[[[(4,6-dimethoxy-2-pyrimidinyl)amino]carbonyl]amino]sulfonyl]methyl]benzoic acid (bensulfuron), 2-[[[[(4,6-dimethoxy-2-pyrimidinyl)amino]carbonyl]amino]sulfonyl]-1-methyl-1 H-pyrazol-4-carboxylic acid (pyrazosulfuron), 3-[[[[(4-methoxy-6-methyl-1,3,5-triazin-2-yl)amino]carbonylamino]sulfonyl]-2-thiophenecarboxylic acid (thifensulfuron), and 2-(2-chloroethoxy)-N-[[(4-methoxy-6-methyl-1,3,5-triazin-2-yl)amino]carbonyl]benzenesulfonamide (triasulfuron); 2-(4aryloxyphenoxy)alkanoic acid herbicides, such as (+/−)-2-[4-[(6-chloro-2-benzoxazolyl)oxy]phenoxy]propanoic acid (fenoxaprop), (+/−)-2-[4-[[5-(trifluoromethyl)-2-pyridinyl]oxy]phenoxy]propanoic acid (fluazifop), (+/−)-2-[4-(6-chloro-2-quinoxalinyl)oxy]phenoxy]propanoic acid (quizalofop), and (+/−)-2-[-(2,4-dichlorophenoxy)phenoxy]propanoic acid (diclofop); benzothiadiazinone herbicides, such as 3-(1-methylethyl)-1H-2,1,3-benzothiadiazin-4(3H)-one 2,2-dioxide (bentazone); 2-chloroacetanilide herbicides, such as N-(butoxymethyl)-2-chloro-2',6'-diethylacetanilide (butachlor); arenecarboxylic acid herbicides, such as 3,6-dichloro-2-methoxybenzoic acid (dicamba); and pyridyloxyacetic acid herbicides, such as [(4-amino-3,5-dichloro-6-fluoro-2-pyridinyl)oxy]acetic acid (fluroxypyr).

It is apparent that various modifications may be made in the formulation and application of the compounds of this invention without departing from the inventive concepts herein as defined in the claims.

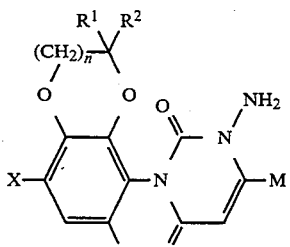

| n | X | Y | R¹ | R² | M |
|---|---|---|---|---|---|
| 1 | 0 | Cl | H | CH₃ | CH₃ | CF₃ |
| 2 | 0 | Cl | F | CH₃ | CH₃ | CF₃ |
| 3 | 0 | Cl | Cl | CH₃ | CH₃ | CF₃ |
| 4 | 0 | Br | F | CH₃ | CH₃ | CF₃ |
| 5 | 0 | CN | F | CH₃ | CH₃ | CF₃ |
| 6 | 1 | Cl | H | H | H | CF₃ |
| 7 | 1 | Cl | Cl | H | H | CF₃ |
| 8 | 1 | Cl | F | H | H | CF₃ |
| 9 | 1 | Br | F | H | H | CF₃ |
| 10 | 1 | CN | F | H | H | CF₃ |

I claim:

1. A compound of the formula:

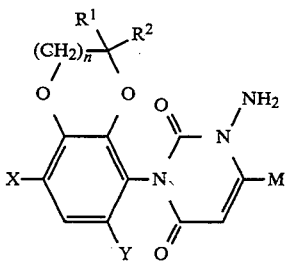

in which

M is fluoroalkyl($C_{1-6}$); $R^1$ is hydrogen or alkyl($C_{1-6}$); $R^2$ is hydrogen or alkyl ($C_{1-6}$); Y is hydrogen, fluorine, chlorine, or bromine; X is hydrogen, fluorine, chlorine, bromine, cyano, alkyl($C_{1-6}$), or fluoroalkyl($C_{1-6}$); and n is 0 or 1.

2. A compound of claim 1 in which M is fluoroalkyl($C_{1-3}$); $R^1$ is hydrogen or alkyl($C_{1-3}$); $R^2$ is hydrogen or alkyl ($C_{1-3}$); Y is hydrogen, fluorine, chlorine, or bromine; X is hydrogen, fluorine, chlorine, bromine, cyano, alkyl($C_{1-3}$), or fluoroalkyl($C_{1-3}$); and n is 0 or 1.

3. A compound of claim 2 in which M is fluoromethyl or fluoroethyl; $R^1$ is hydrogen, methyl, or ethyl; $R^2$ is hydrogen, methyl, or ethyl; Y is hydrogen, fluorine, chlorine, or bromine; X is hydrogen, fluorine, chlorine, bromine, cyano, methyl, or fluoromethyl; and n is 0 or 1.

4. A compound of claim 3 in which M is trifluoromethyl or pentafluoroethyl; $R^1$ is hydrogen, methyl, or ethyl; $R^2$ is hydrogen, methyl, or ethyl; Y is hydrogen, fluorine, or chlorine; X is chlorine or bromine; and n is 0 or 1.

5. A compound of claim 4 in which M is trifluoromethyl; $R^1$ is hydrogen or methyl; $R^2$ is hydrogen or methyl; X is chlorine or bromine; Y is hydrogen, fluorine, or chlorine; and n is 0 or 1.

6. The compound of claim 1 which is 1-amino-3-(7-chloro-2,2-dimethyl-5-fluoro-1,3-benzodioxol-4-yl)-6-trifluoromethyluracil.

7. The compound of claim 1 which is 1-amino-3-(7-bromo-2,2-dimethyl-5-fluoro-1,3-benzodioxol-4-yl)-6-trifluoromethyluracil.

8. The compound of claim 1 which is 1-amino-3-(8-chloro-1,4-benzodioxan-5-yl)-6-trifluoromethyluracil.

9. The compound of claim 1 which is 1-amino-3-(8-bromo-6-fluoro-1,4-benzodioxan-5-yl)-6-trifluoromethyluracil.

10. The compound of claim 1 which is 1-amino-3-(6,8-dichloro-1,4-benzodioxan-5-yl)-6-trifluoromethyluracil.

11. The compound of claim 1 which is 1-amino-3-(7-chloro-2,2-dimethyl-1,3-benzodioxol-4-yl)-6-trifluoromethyluracil.

12. A composition comprising an herbicidally effective amount of a compound of claim 1 in admixture with an agriculturally acceptable carrier.

13. A method for controlling undesired plant growth which comprises applying to a locus where control is desired, an herbicidally effective amount of the composition of claim 12.

* * * * *